(12) United States Patent
Martin et al.

(10) Patent No.: US 6,998,845 B2
(45) Date of Patent: Feb. 14, 2006

(54) PROCESS AND DEVICE FOR ASSESSING THE PERMEABILITY OF A ROCK MEDIUM

(75) Inventors: Jean-Pierre Martin, Le Vaudreuil (FR); Jean-Pierre Pozzi, Meudon (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 112 days.

(21) Appl. No.: 10/469,943

(22) PCT Filed: Mar. 12, 2002

(86) PCT No.: PCT/EP02/02785

§ 371 (c)(1),
(2), (4) Date: Jan. 7, 2004

(87) PCT Pub. No.: WO02/073166

PCT Pub. Date: Sep. 19, 2002

(65) Prior Publication Data

US 2004/0100264 A1    May 27, 2004

(30) Foreign Application Priority Data

Mar. 13, 2001 (FR) .................................. 01 03360
Apr. 18, 2001 (FR) .................................. 01 05223

(51) Int. Cl.
G01V 3/08 (2006.01)

(52) U.S. Cl. ...................................... 324/346; 324/353
(58) Field of Classification Search ................ 324/346, 324/353, 340, 344, 345, 351, 377; 73/152.01–152.11; 166/250.01, 250.02, 252.5
See application file for complete search history.

(56) References Cited

U.S. PATENT DOCUMENTS 5,724,311 A * 3/1998 Laurent et al. ................ 367/57
6,253,848 B1 * 7/2001 Reimers et al. .......... 166/254.1

* cited by examiner

*Primary Examiner*—Bot Ledynh
*Assistant Examiner*—Reena Aurora
(74) *Attorney, Agent, or Firm*—Victor H. Segura; Brigitte L. Echols

(57) ABSTRACT

The present invention relates to the processes and devices for assessing the permeability of a rock medium 1 containing a fluid 2 in its interstices 3. The device and the process according to the invention are characterized essentially in that a given magnetic field is applied to the interstitial fluid 2 located in the rock medium 1, the variation in pressure of the interstitial fluid 2 resulting from the application of the magnetic field is measured, and the permeability of the rock medium is determined as a function of the value of the variation in pressure of the interstitial fluid.

5 Claims, 1 Drawing Sheet

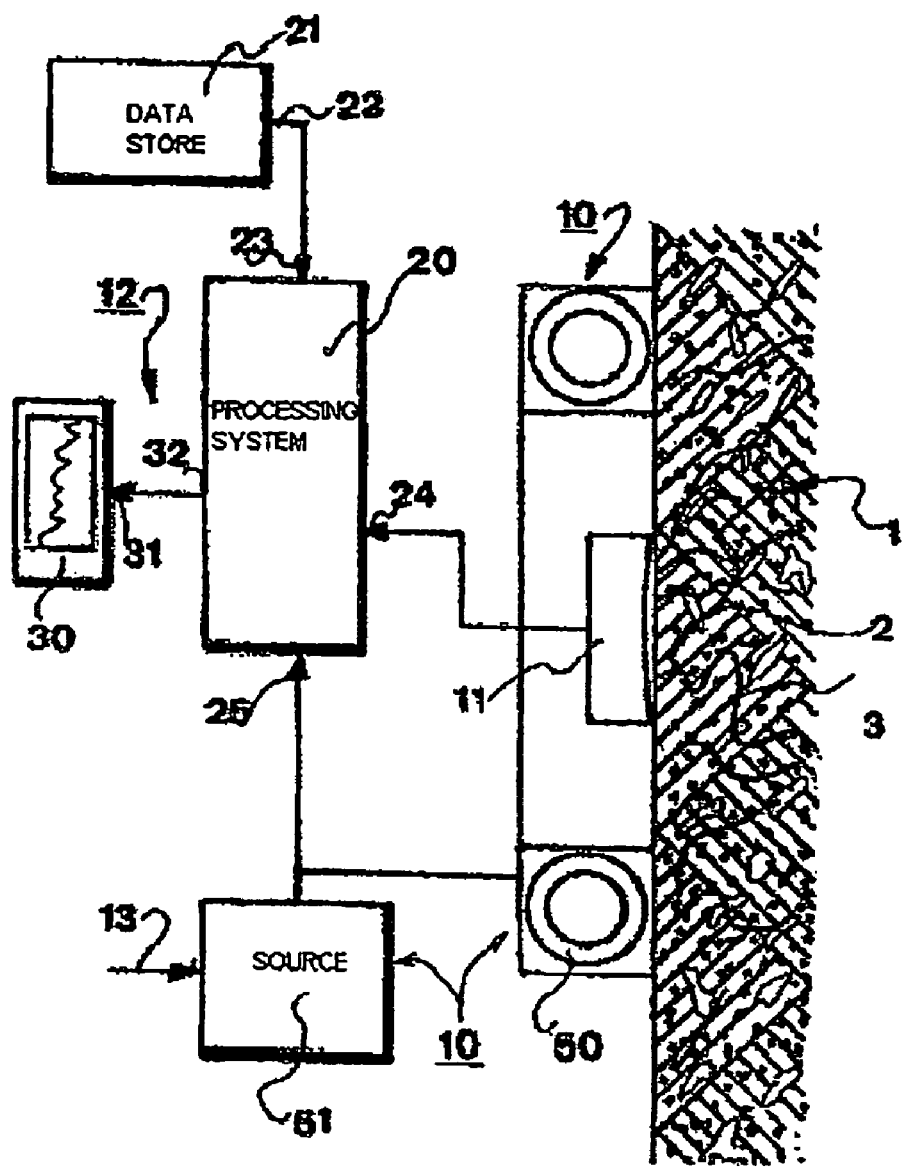

PROCESS AND DEVICE FOR ASSESSING THE PERMEABILITY OF A ROCK MEDIUM

The present invention relates to improved processes and devices for assessing the permeability of a rock medium, which find a particularly advantageous application in determining in situ the permeability of a geological formation surrounding an oil well for example.

It is known that oil and natural gas is extracted from wells drilled in oil-fields which are found in many soil and sub-soil types not all of which have the same production quality. This quality depends mainly on the amount of available, but also recoverable, oil and therefore, particularly but not exclusively, on the rock medium in which it is trapped, i.e. the ease with which the oil is able to flow to the well for subsequent extraction using technologies which are known per se.

It is therefore easy to conceive the importance of being able to know or assess the permeability of any geological formation likely to be the seat of exploitation of a deposit of a fluid, for example oil or natural gas.

One of the first known processes for assessing the permeability of a rock medium consisted in using cores of this medium, then in analysing these cores in the laboratory. This process had many drawbacks, in particular the fact that it was very difficult to deduce the real value of the permeability of the rock medium from the result of measurements taken in the laboratory.

In order to overcome this drawback, an attempt has been made to implement processes and to make devices to try to measure the permeability of a rock medium in situ.

From the document U.S. Pat. No. 4,427,944, are known particularly a process and a device which allow the permeability of a rock medium to be assessed in situ, for example at the bottom of an oil well. The process which is described in this document consists in positioning, in contact with the lateral wall of the well and approximately at a point located at the level where the permeability is to be measured, an excitation source, in controlling this source in such a way that it produces a transitory electrokinetic potential in the rock medium around the contact point, in measuring the amplitude of this electrokinetic potential, in determining a characteristic signal as a function of the response time of this electrokinetic potential created in the rock medium, and in determining the permeability of this rock medium around the contact point as a function of the characteristic signal.

The device allowing this process to be implemented is essentially constituted by a tool capable of creating a transitory electrokinetic potential in the rock medium, means to position this tool in contact with the well wall approximately at a point located at the level of the rock medium where it is wished to measure the permeability, means to control the tool so that it produces an excitation capable of actually realising the transitory electrokinetic potential, at least two electrodes placed against the well wall on either side of the excitation point so as to measure the electrokinetic potential, and means to process the signal delivered by these electrodes in order to determine the permeability of the rock medium at the excitation point.

This process and this device have the advantage of allowing the permeability of geological formations to be measured in situ in wells drilled in these geological formations, but also have, particularly, the following drawbacks. A generally significant spontaneous potential background noise surrounds the electrokinetic potential to be detected, when the latter is still very small. The contact of the electrodes with the well wall must be consistent and excellent, which is very difficult given the geometry of drilling, and the presence of mud in the well may create parasitic impedances between the electrodes and the wall. Consequently, even when it is theoretically possible, measuring the electrokinetic potential is not reliable and the test results supplied by the means for processing the signals delivered by the electrodes are distorted.

Another process has also been perfected, which is described in the document U.S. Pat. No. 5,519,322. This process consists in filling the interstices which can be found in the rock medium with a given fluid, then in transmitting to the interstitial fluid a relative movement in relation to the rock medium, and in measuring the magnetic field produced by the relative movement of the interstitial fluid in the rock medium, so as finally to determine the permeability of the rock medium as a function of the measured magnetic field.

This latter process and the device which allows it to be implemented give good results but, in some circumstances, do not allow a deep enough investigation of the rock medium. Moreover, the device has despite everything a relatively complex structure which is difficult to implement for example at the bottom of an oil well.

The purpose of the present invention is therefore to implement a process for assessing in situ the permeability of a rock medium, which gives better results than the prior art processes set out above.

Another purpose is to make a device enabling the process according to the invention to be implemented, which has particularly a more straightforward structure which is easier to use than prior art devices.

More exactly the object of the present invention is a process allowing assessment of the permeability of a rock medium, characterised in that it consists in filling the interstices which can be found in the rock medium with a given fluid, in applying to said interstitial fluid a given magnetic field, in measuring the variation in pressure of the interstitial fluid resulting from the application of said magnetic field, and in determining the permeability of the rock medium as a function of the value of the variation in pressure of said interstitial fluid.

A further object of the present invention is a device for assessing the permeability of a rock medium containing a fluid in its interstices, characterised in that it comprises means for applying a magnetic field to the interstitial fluid located in the rock medium, means for measuring the variation in pressure of the interstitial fluid resulting from applying said magnetic field, and means for determining the permeability of the rock medium as a function of the value of the variation in pressure of said interstitial fluid.

Other characteristics and advantages of the invention will emerge during the following description given with reference to the appended drawing as an in no way restrictive illustration, wherein:

The single figure shows, in diagrammatic form, an embodiment of a device according to the invention allowing the permeability of a rock medium to be assessed in situ, in an application to a well in an oil or natural gas deposit.

The Applicants wish to state that the figure shows in a diagrammatic way one embodiment of the object according to the invention, but that other embodiments may exist which meet the definition of this invention.

They additionally state that, when, according to the definition of the invention, the object of the invention comprises "at least one" element having a given function, the embodiment described may comprise several of these elements.

They further state that, if the embodiment as illustrated comprises several elements with an identical function and that if, in the description, it is not stated that the object according to this invention must mandatorily comprise a particular number of these elements, the object of the invention shall be able to be defined as comprising "at least one" of these elements.

The present invention concerns a process allowing the assessment of the permeability of a rock medium, for example an oil bearing medium or the like lining the wall of a well drilled in this rock medium.

The process consists first of all, if it is not done beforehand or in a natural way, in filling the interstices which can be found in the rock medium with a given fluid, like for example water or any other fluid adapted to fill these interstices.

It then consists in applying to this interstitial fluid a given magnetic field, the value of which will be defined essentially experimentally to obtain the best results, then in measuring the variation in pressure of the interstitial fluid resulting from applying the magnetic field, for example the difference between the value of this pressure before the application of the magnetic field and that during the application of this magnetic field.

The pressure variations may be measured by means of a pressure sensor placed directly in the interstitial fluid.

However, this possibility is very unusual, particularly in the application to measuring the permeability of a rock medium at the bottom of an oil well. Also, according to the present invention, it is to advantage possible to determine these pressure variations from the measurements of variations in pressure of the seismic waves which result when the interstitial fluid is itself subjected to a pressure variation, particularly a variable one, by application of a magnetic field as mentioned above. Indeed, when the interstitial fluid is subjected to a pressure variation, it is subjected to a shock which creates a seismic wave which is transmitted throughout the surrounding medium, the rock, the interstitial fluid and the fluid which is generally found at the bottom of the well.

All that is therefore required is to place hydrophones, for example, in the fluid contained in the bottom of the well and to read the variations in pressure recorded by these hydrophones which pick up the seismic waves defined above.

It is moreover pointed out that, when a seismic wave is produced, it breaks down into two components which those skilled in the art name respectively "pressure wave P" and "shear wave S".

In an advantageous way, by placing the hydrophones in the fluid present in the bottom of the well, a measurement is obtained on the P waves, but it is also possible, by placing a wall seismograph or the like against the well wall, to obtain a significant measurement of the pressure variation by measuring the S waves.

The pressure variations of the interstitial fluid are obtained from measurements of pressure variations taken on the seismic waves, particularly by means of graphs obtained by experimentation.

The process consists lastly in determining the permeability of the rock medium as a function of the value of the variation in pressure of the interstitial fluid determined according to one of the methods described above, it being understood that the man skilled in the art will choose one or other of these methods as a function particularly of the nature of the rock medium, the environment and the ease of access.

When seeking to assess the as yet unknown permeability of a rock medium, by implementing this process, all that is required is to measure the variation in pressure of the interstitial fluid resulting from the application of the magnetic field in this rock medium, then, for example, to interrogate experimentally obtained databanks, which deliver at their output the permeability value corresponding to the value of the variation in pressure of the interstitial fluid which has been measured, the permeability value being obtained directly or by extrapolation relative to the permeability values stored in these data banks. The values pre-entered in these databanks The process described above therefore makes it possible to assess the permeability of a rock medium in the vicinity of the points at which a given magnetic field is applied.

To assess the permeability of the rock medium in its entirety, for example along a well drilled in this rock medium, the process according to the invention is applied a plurality of times, along this well.

In this case however it is not mandatorily necessary to interrogate the databanks as mentioned above after measuring the variation in pressure resulting at each point along the well.

It may indeed be enough to know the permeability value at at least one point of this rock medium and then to measure, at other points along the well, only the pressure variations.

Likewise, if it is enough to know only the variation in the permeability of the rock medium around a well, it will be enough to compare the variations in pressure of the interstitial fluid caused by the magnetic field as measured along the well or well portion under investigation.

The process described above is to advantage implemented by a device one embodiment of which is shown diagrammatically in the single FIGURE.

This device, allowing assessment of the permeability of a rock medium 1 containing a fluid 2 in its interstices 3, comprises means 10 for applying a given magnetic field to the interstitial fluid 2, means 11 for measuring the variation in pressure of the interstitial fluid 2 resulting from applying the magnetic field, and means 12 for determining the permeability of the rock medium as a function of the value of the variation in pressure of the interstitial fluid.

In one possible embodiment, the means 11 for measuring the variation in pressure of the interstitial fluid resulting from applying the magnetic field are constituted by a differential membrane sensor, or even if that is possible for example by a strain gauge needle sensor which may thus penetrate inside the rock medium 1.

As for the means 10 for applying a given magnetic field to the interstitial fluid 2 located in the rock medium 1, they are preferably constituted by at least one of the following elements: one or more magnetic coils 50 with their feeds 51, at least one permanent magnet, a combination of a coil and a permanent magnet, etc.

In one advantageous embodiment, when the means 10 for applying the magnetic field are constituted by a magnetic coil or the like, the means 11 for measuring the variation in pressure of the interstitial fluid resulting from the application of this magnetic field are provided so as preferentially to measure this pressure variation on the axis of the magnetic coil as shown diagrammatically in the single figure.

It may also be expected, for some applications, that the device additionally comprises means 13 for modulating the value of the magnetic field. These means may for example be constituted by means for modulating the value of the electric current delivered by the power source or sources 51.

The means 12 for determining the permeability of the rock medium 1 as a function of the value of the variation in pressure of the interstitial fluid resulting from the magnetic field applied to this fluid, comprise at least one processing system 20, for example based on a micro-processor, a store of pre-set data 21 corresponding to permeability values of rocks as a function of variations in pressure of the interstitial fluid in these rocks for given magnetic field values, the output 22 of the memory being connected to a first control input 23 of the processing system, this processing system comprising two other second 24 and third 25 control inputs receiving the values of the applied magnetic field and of the measured pressure variation respectively.

It is also possible for the means 12 for determining the permeability of the rock medium as a function of the value of the variation in pressure of the interstitial fluid to comprise additionally a permanent memory 30, such as a recorder or the like, the input 31 of which is connected to an output 32 of the processing system 20.

The device as described above has advantages relative to those of the prior art. Indeed, with such a device, it is not necessary to provide means for controlling a modulation of the pressure of the interstitial fluid, but only cables, for example to supply power to the coil 50, in order to measure variations in pressure of the interstitial fluid etc.

Clearly, the device, as described above in its application to measuring the permeability of rocks along a well, will be combined with a tool well known per se, particularly in the oil area.

What is claimed is:

1. A process allowing the permeability of a rock medium to be assessed, characterized in that it consists: in filling the interstices which can be found in the rock medium with a given fluid, in applying to said interstitial fluid a given magnetic field, in measuring the variation in pressure of the interstitial fluid resulting from the application of said magnetic field, and in determining the permeability of the rock medium as a function of the value of the variation in pressure of said interstitial fluid.

2. A process according to claim 1, characterized in that the variation in pressure of the interstitial fluid resulting from the application of said magnetic field is determined from the measurement of the variation in pressure of the seismic wave resulting from said variation in pressure of the interstitial fluid.

3. A process according to claim 2, characterized in that the variation in pressure of the seismic wave is measured on at least one of the two component parts of the seismic wave, namely the pressure wave P and the shear wave S.

4. A device for assessing the permeability of a rock medium (1) containing a fluid (2) in its interstices (3), by applying the process according to one of the claims 1 to 3, characterized in that it comprises: means (10) for applying a given magnetic field to the interstitial fluid (2) located in the rock medium, means (11) for measuring the variation in pressure of the interstitial fluid (2) resulting from the application of said magnetic field, and means (12) for determining the permeability of the rock medium as a function of the value of the variation in pressure of the interstitial fluid.

5. A device according to claim 4, characterized in that the means (11) for measuring the variation in pressure of the interstitial fluid resulting from the application of said magnetic field are constituted by a differential membrane sensor.

* * * * *